United States Patent
Stupperich et al.

(10) Patent No.: US 7,569,041 B2
(45) Date of Patent: Aug. 4, 2009

(54) DISPOSABLE DIAPER WITH A HIP BELT

(75) Inventors: Hans-Peter Stupperich, Heidenheim (DE); Wolfgang Roehrl, Herbrechtingen (DE); Matthias Bandorf, Schweinfurt (DE)

(73) Assignee: Paul Hartmann AG, Heidendeim (DE)

( * ) Notice: Subject to any disclaimer, the term of this patent is extended or adjusted under 35 U.S.C. 154(b) by 477 days.

(21) Appl. No.: 10/566,175

(22) PCT Filed: May 11, 2004

(86) PCT No.: PCT/EP2004/005012

§ 371 (c)(1),
(2), (4) Date: Jan. 27, 2006

(87) PCT Pub. No.: WO2005/023161

PCT Pub. Date: Mar. 17, 2005

(65) Prior Publication Data

US 2006/0184152 A1    Aug. 17, 2006

(30) Foreign Application Priority Data

Aug. 6, 2003   (DE) ................... 103 37 537

(51) Int. Cl.
*A61F 13/15* (2006.01)
(52) U.S. Cl. .............. 604/392; 604/391; 604/386; 604/387; 604/385.26; 604/385.29; 604/385.3; 604/396
(58) Field of Classification Search ............ 604/392, 604/385.26, 385.27, 385.29, 385.3, 386, 604/387, 389, 394, 396, 391
See application file for complete search history.

(56) References Cited

U.S. PATENT DOCUMENTS

| 5,135,522 A | 8/1992 | Fahrenkrug |
| 5,318,555 A | 6/1994 | Odorzynski |

(Continued)

FOREIGN PATENT DOCUMENTS

DE    197 32 499    2/1999

(Continued)

*Primary Examiner*—Jacqueline F. Stephens
(74) *Attorney, Agent, or Firm*—Paul Vincent

(57) ABSTRACT

The invention relates to a disposable diaper (2), used more particularly in the event of incontinence, comprising a hip band (10) forming a hip opening in the diaper which is closed in the direction of the periphery whereby said hip band can be opened in at least one place and can be closed, also comprising a front area, a rear area and a main diaper part (4) which has a crotch area located there between and which comprises an absorbing body (6) for liquids. The main part (4) of the diaper can be detachably fixed to the hip band using the longitudinal end of the front area or rear area, by means of first closing means (34) such that a user can place the main part (4) of the diaper between his/her legs when the hip band is worn (10) and can detachably fix the free longitudinal end of the main part (4) of the diaper to the hip band (10). The hip band (10) is made of a single-pieced material section (8) which is added to the main part (4) of the diaper and which is folded on the two sides of a longitudinal center axis around two fold lines (20) extending in the longitudinal direction (18) of the diaper.

11 Claims, 3 Drawing Sheets

U.S. PATENT DOCUMENTS

| | | |
|---|---|---|
| 6,413,246 B1 | 7/2002 | Harrold |
| 2001/0034512 A1 | 10/2001 | Hermansson |
| 2002/0045881 A1 | 4/2002 | Kusibojoska |

FOREIGN PATENT DOCUMENTS

| | | |
|---|---|---|
| EP | 0 206 208 | 12/1986 |
| EP | 0 287 388 | 10/1988 |
| EP | 0 605 012 | 7/1994 |
| EP | 0 605 013 | 7/1994 |
| EP | 0 605 014 | 7/1994 |
| EP | 0 617 941 | 10/1994 |
| EP | 1 110 529 | 6/2001 |
| EP | 0 941 041 | 1/2002 |
| EP | 1 269 949 | 1/2003 |
| WO | WO 91/08725 | 6/1991 |
| WO | WO 97/33547 | 9/1997 |
| WO | WO 98/20824 | 5/1998 |
| WO | WO 98/37847 | 9/1998 |
| WO | WO 98/48750 | 11/1998 |
| WO | WO 02/22062 | 3/2002 |
| WO | WO 02/22063 | 3/2002 |
| WO | WO 02/22064 | 3/2002 |
| WO | WO 02/49568 | 6/2002 |
| WO | WO 02/094165 | 11/2002 |
| WO | WO 03/007863 | 1/2003 |
| WO | WO 03/009794 | 2/2003 |
| WO | WO 03/015685 | 2/2003 |
| WO | WO 03/017903 | 3/2003 |
| WO | WO 03/017904 | 3/2003 |

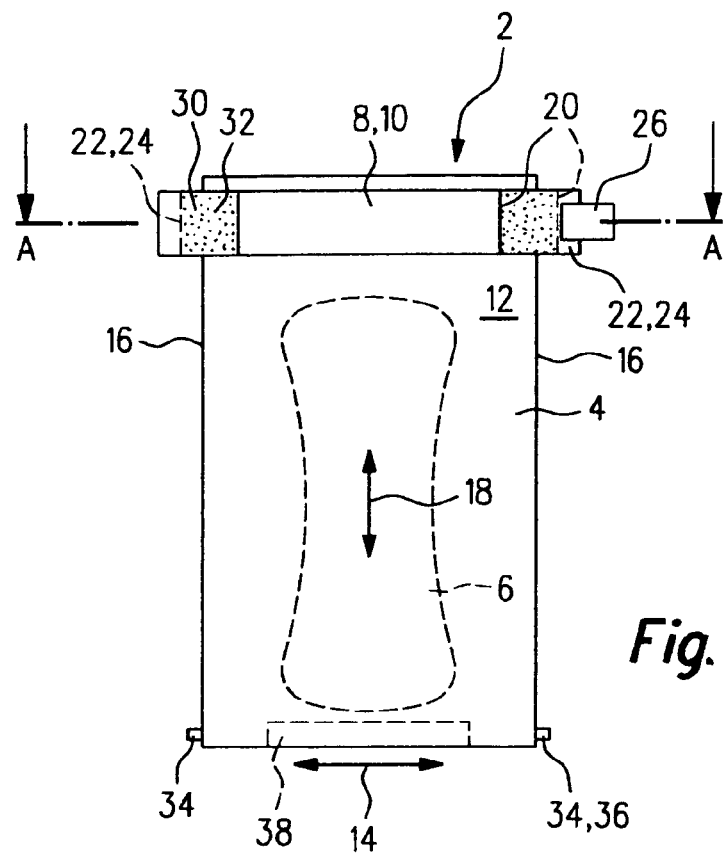
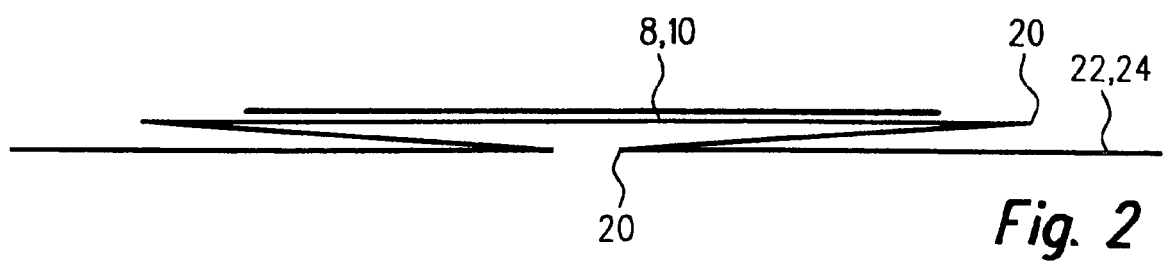
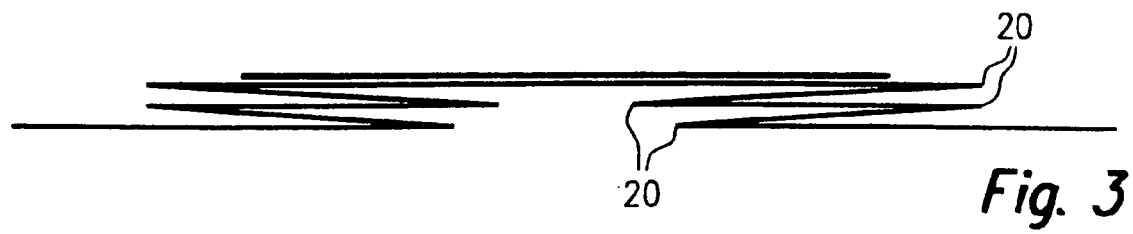

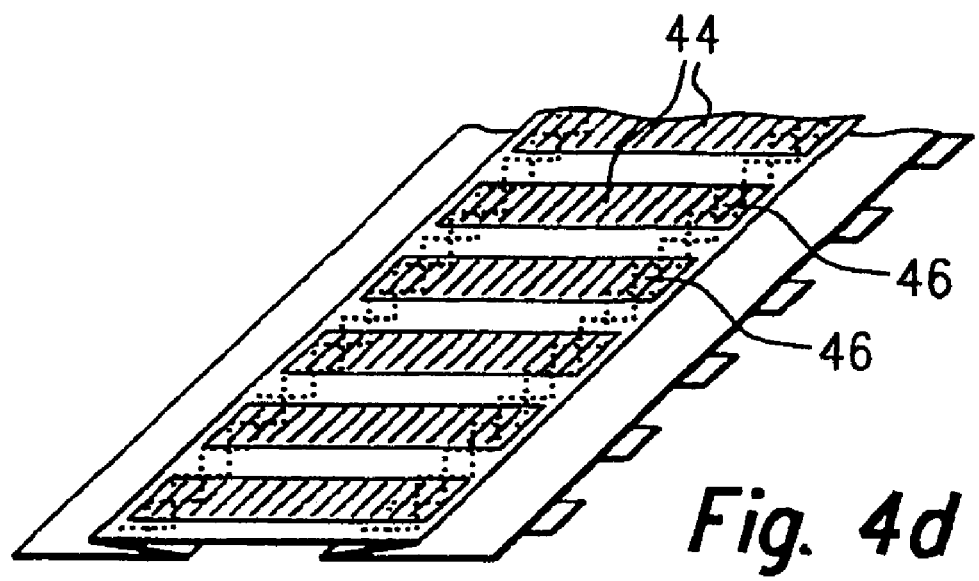
Fig. 4d
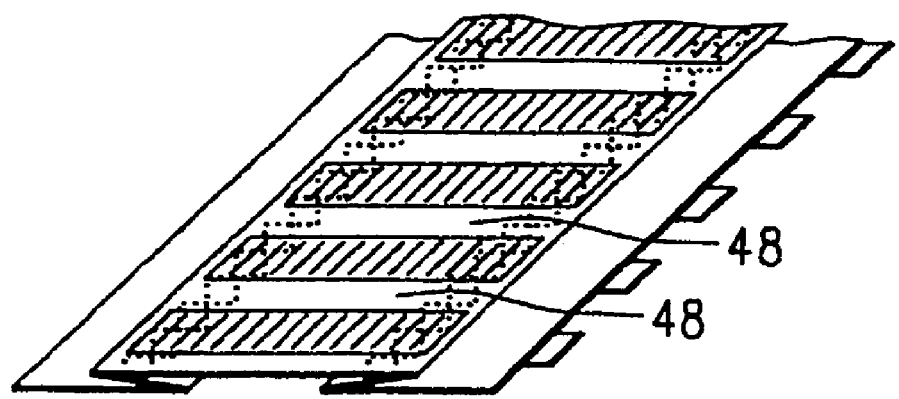
Fig. 4e

DISPOSABLE DIAPER WITH A HIP BELT

This application is the national stage of PCT/EP2004/005012 filed on May 11, 2004 and also claims Paris Convention priority of DE 103 37 537.6 filed on Aug. 6, 2003.

BACKGROUND OF THE INVENTION

The invention concerns a disposable diaper, in particular for incontinent care, having a diaper hip opening forming a hip belt and extending in a closed fashion in a peripheral direction which can be opened and closed onto itself at least one location, and with at least one main diaper section having a front region, a back region and an intermediate crotch region and having an absorption body for liquids, wherein the main diaper section can be attached to the hip belt in a detachable fashion at a longitudinal end of its front region or of its rear region via a first closing element in such a fashion that the user, with the applied hip belt, can lift the main diaper section between the legs and attach the free longitudinal end of the diaper main section to the hip belt in a detachable fashion.

A disposable diaper of this type is e.g. disclosed in US 2001/00 34 512 A1 or EP12 69 949 A2.

Disposable diapers of this type have been described a plurality of times in the art. They have the advantage that, when applying the diaper, the user can first dispose the hip belt about the hips and usually enclose the stomach region. At this point, the main diaper portion usually hangs at its rear region from a portion attached to the belt such that the disposable diaper hangs loosely in a downward direction. With the hip belt closed, the user grasps the freely hanging end of the main diaper section and guides the main diaper section between the legs in a forward direction to attach the free longitudinal end of the main diaper section to the inside or outside of the hip belt using first closing elements provided for this purpose. Clearly, application of the disposable diaper can also be carried out in such a fashion that, after attaching and closing the hip belt, the free downwardly hanging diaper section is guided from the front towards the rear between the legs of the user and attached at the rear region to the hip belt in a detachable fashion. Disposable diapers have also been known in the art with which the main diaper section can be completely removed from the hip belt so that, in particular for users in need of intensive nursing care and immobile users, great flexibility is guaranteed for handling of the disposable diaper.

In the above-mentioned publications, a separate transverse material section is joined to each side of the main diaper section to form the hip belt. Since large forces act on the belt during proper use of the diaper, these forces must be properly introduced into and accepted by the main diaper section.

It is the underlying purpose of the present invention to improve a disposable diaper of the above mentioned kind with regard to the problems mentioned above while effecting economical manufacture thereof. Moreover, a suitable manufacturing procedure should also be created.

SUMMARY OF THE INVENTION

This purpose is achieved in accordance with the invention with a disposable diaper of the above mentioned kind in that the hip belt is formed from a single piece of material section which is joined onto the main diaper section and which is folded onto itself at fold lines extending in a longitudinal direction of the diaper on each of both sides of a longitudinal middle axis thereof.

In accordance with the invention, a single piece material section extending in the transverse direction or in the peripheral direction is attached to the main diaper section to form a hip belt. Due to the attachment over a wide area, the tensile forces are not introduced directly into the main diaper section, rather can be completely accepted from the tear-resistant belt material. This permits greater flexibility in the choice for the chassis material forming the main section. Moreover, the requirements concerning the strength with which the belt is attached to the main section are reduced. As will be described more closely below with reference to a manufacturing procedure in accordance with the invention, the material section forming the belt can be obtained from one single longitudinal section of a flat material web introduced in a machine direction.

In a further advantageous configuration of the concept underlying the instant invention, the hip belt is fixed in a detachable fashion in its two-sided, folded configuration so that it cannot be unintentionally unfolded or flattened out within the rapidly processing manufacturing machine. The detachable fixing of the hip belt in the folded configuration advantageously facilitates introduction of the very long hip belt onto the main section within the production machine.

In a further advantageous improvement of the concept underlying the invention, the detachable fixing among the folded-together partial section of the material piece forming the hip belt is effected through binding locations or binding regions. It is also possible to fix the folded configuration in a detachable fashion using other holding means, such as a detachable tape section.

The above mentioned detachable fixation of the folded together partial sections of the hip belt introduced on the main section as a material section is preferably effected in a single step, e.g. through cold stamping or through stamping while applying heat (thermal welding), through needle perforation procedures, in particular hot needle perforation, or through ultrasound welding, laser welding or some similarly effective joining method.

In the simplest case, the material section is folded onto itself about a fold line on each side of the longitudinal middle axis so that two partial sections seat upon each other. However, the material section is preferentially folded onto itself about at least two fold lines so that, in section, a Z-shaped configuration is formed. In accordance with an additional preferred embodiment, the material sections are folded upon themselves about three fold lines. In accordance with an additional preferred embodiment, the material sections are folded upon themselves about four fold lines.

In accordance with an additional preferred embodiment of the belt diaper in accordance with the invention in its folded configuration, the one piece material section exhibits a grasping region at its free end which projects in the transverse direction past a longitudinal side edge of the main diaper section. Corresponding free ends of the hip belt can in particular, form the grasping region.

It has turned out to be particularly advantageous if, prior to unfolding of the single piece material section, the grasping regions are preferentially turned transversely in an outer direction and widened with respect to each other on a flat surface away from a longitudinal middle axis of the main diaper section so that they can easily be grasped with the left hand of the user from the left side and with the right hand of the user from the right side, in particular, for use with patients in need of intensive nursing care. Towards this end, the belt diaper is often used on patients in need of nursing care at a position in which the patient is lying on his/her side. The material section protruding past the main section must then be introduced below and past the patient. This procedure of threading below and past the patient is particularly easy with a folded belt material section, which is fixed, in a detachable fashion.

The detachable fixing of the mutually folded partial sections of the material section and optionally to the main section, is preferentially formed through a plurality of substantially point-like joining locations. A point-like joining location of the above mentioned kind means that the joining location has a surface (projected onto the X-Y plane of the main section) of less than 5 mm², in particular of less than 2 mm² and most particularly of less than 1 mm². The joining locations must not be strictly point or circular shaped. Shapes that deviate from a point or circular shape such a triangular, rectangular, polygonal or oval are also conceivable and advantageous. The detachable fixing of the folded partial sections of the material sections seating upon each other is preferentially produced through heat or ultrasound, preferentially forming point-like fixing locations.

The transverse extent of the material section forming the hip belt past the longitudinal edge of the main section in the unfolded state assumes values of at least 200 mm, in particular at least 300 mm, in particular at least 400 mm, in particular at least 500 mm, in particular at least 600 mm. Its extent in the longitudinal direction assumes values of 30 to 120 mm, in particular 30 to 100 mm, in particular 30 to 80 mm, in particular 30 to 75 mm, in particular between 44 and 70 mm, in particular between 40 and 65 mm and in particular from 40 to 60 mm.

The one-piece material section is preferentially permanently attached to the outer side of the main section. This attachment can be carried out in an arbitrary manner. The single piece material section can advantageously be joined to the main diaper section through the application of glue at certain areas only. In particular, it has turned out to be advantageous when the glue does not extend up to the edge of the mutually seated wide area extent of the material section and the associated main section so that a peripheral edge region of the composite remains free of glue. This has the advantage, that in the event of lamination, no glue can gain entrance between the layers and be pushed outwardly.

The invention also concerns a method for the production of a disposable diaper of the above-mentioned kind. This method is characterized by the following method steps:
   introducing a continuous, flat material web for formation of material section to produce the hip belt;
   folding the flat material web on top of itself about fold lines extending in the longitudinal direction at both sides of a longitudinal middle axis;
   separating longitudinal sections of a folded flat material web for corresponding formation of a one piece material section for the production of the hip belt; and
   permanent fixing or attachment of the material section to a main diaper section.

Preferred embodiments of the method in accordance with the invention can be derived from the dependent claims. In particular, it has turned out to be advantageous in the event that the single piece material section forming the hip belt is attached to the main diaper section using glue. It has also turned out to be advantageous when the glue is introduced onto the flat material web and is separated into the material sections in regions, which are spaced apart from each other in the longitudinal direction. Towards this end, the cut regions are thereby preferentially free of glue.

It has also turned out to be advantageous when the glue is introduced onto the flat material web in sections and in such a fashion that it is spaced apart from an edge of the subsequently separated flat material section in a longitudinal direction and preferentially also in the transverse direction. In this case the glue is advantageously applied to the flat material web in cycles.

The one piece material section introduced onto the main section is preferentially made from a bonded fiber material, in particular or preferentially from spun bond materials (S) or spun bond melt blown materials (SM) or has spun bond materials and melt blown materials (SMS) on both sides, or packages of bonded fiber materials are utilized. Laminated bonded fiber fabrics, in particular, with two layers, three layers or multi-layer combinations of the above mentioned bonded fiber materials can also be utilized. The individual layers can be connected using conventional procedures, for example through thermal joining (welding, in particular laser welding, hot melt, air through) using ultrasound welding procedures or also through cold pressing, needle perforation, sewing or gluing of the bonding fiber fabrics. Composites having textile cloths, weaves and knits, i.e. having material textile combinations of the broadest kinds, are also conceivable. Even films from thermoplastics and in particular elastic materials can be utilized; as well as multiple layer film laminates. Fleece foil laminates can be preferentially utilized which have at least one film layer and at least one bonded fabric layer or at least one layer of a textile material. Film layers are particularly useful for realizing the elastic regions of the hip belt. The layers can also be connected using the above-mentioned procedures.

At least sections of the material section are preferentially made from a material, which breathes, in particular a material having micro pores. This facilitates exchange of air and creates permeability to liquids in vapor form. The material sections preferentially have a surface density of 30 to 150 g/m².

Further features, details and advantages of the invention can be derived from the accompanied patent claims as well as from the drawings and the subsequent description of the preferred embodiment of the diaper in accordance with the invention.

BRIEF DESCRIPTION OF THE DRAWING

FIG. 1 is a schematic representation of a belt diaper with a folded hip belt;

FIG. 2 is a schematic section in cut plane A-A of the belt diaper of FIG. 1 with a first folding of the hip belt;

FIG. 3 is a schematic cut representation in cut plane A-A of the belt diaper of FIG. 1 with a second folding of the hip belt; and FIG. 4a through 4e show, in schematic representations, the introduction, folding, attachment, application of glue, and cutting of a flat material web forming a hip belt section.

DESCRIPTION OF THE PREFERRED EMBODIMENT

Figure 4A:
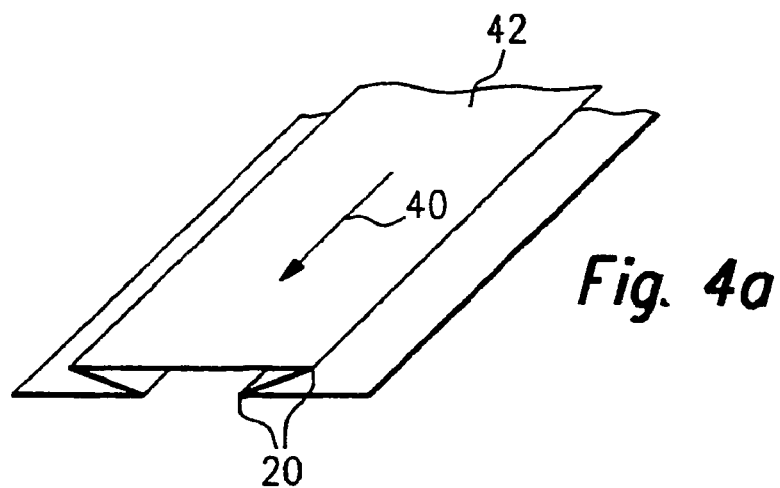

FIG. 1 schematically shows a disposable belt diaper 2 having a main section 4 and with a schematically indicated absorption body 6. A single piece material section 8 is attached to the main section 4 to form a hip belt 10 for the belt diaper. The one-piece material section 8 is permanently attached to an outer side 12 of the main section 4 in a manner, which is described in greater detail below. In the unfolded state, it extends in the transverse direction 14 of the belt diaper 2 past sideward longitudinal edges 16 by at least 300 mm, in particular by at least 400 mm, in particular by at least 500 mm, in particular by at least 600 mm. In the example shown in FIG. 1, the one piece material section 18 is folded onto itself a plurality of times at fold lines 20 extending in a longitudinal direction on each side of the diaper 18. Each of the free ends 22 of the material section 8 form a grasping region 24 for the fingers of the user, which projects past the longitudinal side edges 16 by at least 10 mm. A closing-element 26 is also provided on the free end 22 e.g. in the form of a tap having a gluing or preferentially mechanical closing element which can cooperate with a joining region or cooperating closing element on the other end of the hip belt 22 in a detachable fashion when the hip belt 22 is closed to form a closed hip opening extending peripherally about the hip.

The partial sections 30 of the one piece material section 18 which are folded on top of each other are fixed to each other in a detachable manner through the application of a plurality of substantially point shaped joining sections 32, e.g. using ultrasound welding points.

In order to apply the belt diaper 2, the hip belt 10 is unfolded and closed onto itself using closing elements 26 and the appropriately configured joining regions on the opposite free end of the hip belt 10. The user or a nursing assistant thereby grasps the free end of the main section which hangs in a downward direction, passes it through the legs of the user, and attaches it in a detachable fashion to the ring-shaped closed hip belt 10, preferentially at the outer side of the hip belt 10 facing away from the user. The main portion 4 can, for its part, be fashioned in a detachable manner using arbitrary glued or mechanically locking closing elements 34, in the present case, using closing taps 36 which protrude sidewardly from the main section. Moreover, any type, kind or shape of additional closing elements can be provided, preferentially on the inner side of the main section 4 facing the body of the user at corresponding overlap regions 38.

FIGS. 2 and 3 show different ways of folding the one-piece material section 8 (without showing the closing elements 26). The folding in accordance with FIG. 2 has two folding lines 20 on each side the associated folding is therefore Z-shaped. The overall length of the hip belt 10 (including the transverse extension past the main section i.e. the peripheral length of the entire hip opening) assumes values of approximately 1200 mm (the overlapped region of the closed hip belt 10 is not included in this number). The width of the belt, i.e. its extension in the longitudinal direction 18, is between 50 and 100 mm.

The folding shown in FIG. 3 exhibits a fold line 20 on each side. The entire length of the belt is approximately 1600 mm.

Figure 4B:
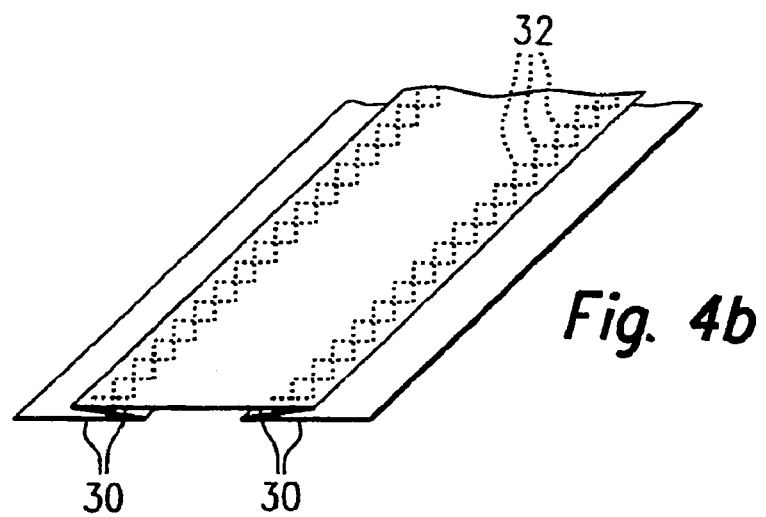
Figure 4C:
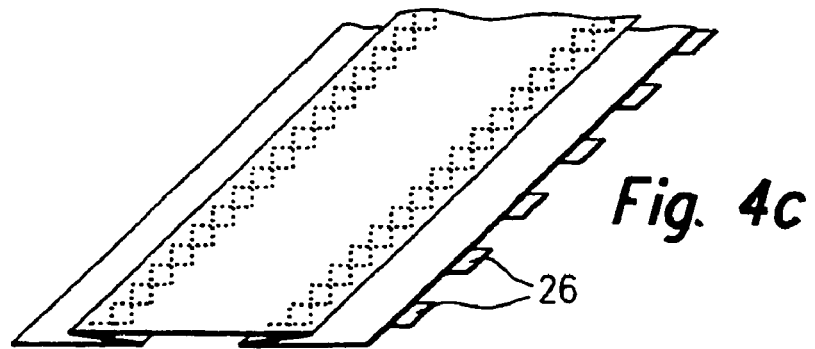

FIGS. 4a through 4e illustrate the method of production of a belt diaper in accordance with the invention in particular with regard to the production of the hip belt 10. Towards this end, a flat material web 42 was introduced in a longitudinal direction of a machine 40. The flat material web 42 is, in the example of FIG. 4a, folded about two fold lines 20 to form a Z-shape. However, folding about 3, 4 or more folding lines is also conceivable. The partial sections 30 folded on top of each other can be attached to each other in a detachable manner as schematically indicated in FIG. 4b. This can advantageously be done using substantially point shaped joining locations 32, in particular using ultrasound welding points. FIG. 4c shows the introduction of closing elements 26 on one side of the flat material web 42.

As can be seen in FIG. 4d, glue 44 can then be applied to certain regions of the flat material web 42 which are spaces apart from each other in the longitudinal direction 40, preferentially using a cycled procedure.

As indicated in FIG. 4e, the longitudinal section 44 is then separated from the continuous flat material web 42 in the longitudinal direction 40, to thereby generate a transverse single piece material section 8 for the hip belt 10. As can be seen in FIG. 4e, the cut is made in regions 48 which are free of glue.

The longitudinal section 47 of the flat material web 42 which is, separated in this fashion can preferentially be permanently attached to the outer side 12 of a main diaper section 44, as shown in FIG. 1 and already described above.

We claim:

1. A disposable diaper for incontinent care, the diaper comprising:
a main diaper section having a front region, a rear region having first and second side regions, and a crotch region disposed between said front region and said rear region, said main diaper section also having an absorption body for liquids and closing means disposed at a first longitudinal end thereof, proximate said front region or said rear region; and a hip belt formed from a single piece material section and joined onto said main diaper section and thereby extends on both of said first and said second side regions, said hip belt defining a diaper hip opening which closes in a peripheral direction, said hip belt structured for opening and closing onto itself at at least one location, said hip belt folded onto itself along folding lines extending in a longitudinal direction on both sides of a longitudinal middle axis of the diaper, wherein said closing means can be secured to said hip belt in a detachable fashion in such a manner that a user, with said hip belt applied and closed, lifts said main diaper section upwardly between the legs to attach a free longitudinal end of said main diaper section to said hip belt in a detachable fashion, wherein said hip belt is fixed in a folded configuration in a detachable fashion, and, in a folded configuration, a grasping region at each of two free ends of said single piece material section protrudes in a transverse direction past a longitudinal side edge of said main diaper section, wherein said single piece material section is attached in a permanent manner to an outer side of said main diaper section with glue to form a composite, wherein the glue does not extend up to the edge of the composite so that a peripheral edge region of the composite remains free of glue.

2. The disposable diaper of claim 1, wherein a detachable fixing between partial sections of said single piece material section forming said hip belt which are folded on top of each other is effected by means of attachment locations or attachment regions.

3. The disposable diaper of claim 2, wherein said attachment locations or attachment regions are substantially point shaped.

4. The disposable diaper of claim 1, wherein said single piece material section is folded onto itself on each side of the longitudinal middle axis of the diaper, about at least two respective fold lines.

5. The disposable diaper of claim 1, wherein the single piece material section is folded onto itself on each side of the longitudinal middle axis of the diaper about three or four respective fold lines.

6. The disposable diaper of claim 1, wherein, in a folded configuration, the grasping region located on each of two free ends of said single piece material section protrudes in a transverse direction past a longitudinal side edge of said main diaper section by at least 10 mm, by at least 20 mm, or by at least 30 mm.

7. The disposable diaper of claim 1, wherein said single piece material section forming said hip belt extends, in an unfolded state, in a transverse direction past a longitudinal edge of said main section by at least 200 mm, by at least 300 mm by at least 400 mm, by at least 500 mm, or by 600 mm.

8. The disposable diaper of claim 1, wherein said hip belt has an extension in a longitudinal direction of 30 to 120 mm, of 30 to 100 mm, of 30 to 80 mm, of 30 and 75 mm, of 44 to 70 mm, of 40 to 65 mm, or of 40 to 60 mm.

9. A method for the manufacturing the disposable diaper of claim 1, the method comprising the steps of:
 a) introducing an endless flat material web to form material sections for manufacturing the hip belt;
 b) folding the flat material web about folding lines extending in a longitudinal direction, wherein the flat material web is folded onto itself at each side of its longitudinal central axis;
 c) introducing glue in sections onto the flat material web in such a fashion that it is spaced apart in a longitudinal direction from an edge of the subsequently separated material section and such that it is spaced apart in a transverse direction from an edge of the subsequently formed separated material section;
 d) separating longitudinal sections of the folded, flat material into respective single-piece material sections for the hip belt; and
 e) permanently fixing the material section onto a main diaper section with the glue previously introduced so that the glue does not extend up to the edge of the composite of the mutually attached wide area extent of the single piece material section and an associated main section area of the back sheet so that a peripheral edge region of the composite remains free of glue.

10. The method of claim 9, wherein the flat material web is folded onto itself at two respective fold lines on each side of the longitudinal axis.

11. The method of claim 9, wherein the partial sections of the flat material web are attached to each other in a detachable fashion.

* * * * *